United States Patent [19]

Celmer et al.

[11] 4,212,944

[45] Jul. 15, 1980

[54] PROCESS FOR PRODUCING NOCARDICIN A

[75] Inventors: Walter D. Celmer, New London; Liang H. Huang, East Lyme; Mark T. Jefferson, Waterford, all of Conn.; Hiroshi Maeda; Kozo Inoue, both of Chita, Japan; Riichiro Shibakawa, Handa, Japan

[73] Assignee: Pfizer Inc., New York, N.Y.

[21] Appl. No.: 45,009

[22] Filed: Jun. 4, 1979

[51] Int. Cl.$^2$ ............................................. C12D 9/14
[52] U.S. Cl. .................................. 435/121; 435/822; 435/872
[58] Field of Search .......................................... 435/121

[56] References Cited

U.S. PATENT DOCUMENTS

| | | | |
|---|---|---|---|
| 3,923,977 | 12/1975 | Aoki et al. | 435/128 X |
| 4,110,166 | 8/1978 | Mori et al. | 435/121 |
| 4,146,536 | 3/1979 | Hosoda et al. | 435/121 X |

Primary Examiner—Lionel M. Shapiro
Attorney, Agent, or Firm—Connolly and Hutz

[57] ABSTRACT

A new species of Nocardiopsis, designated *Nocardiopsis atra* Huang sp. nov. ATCC 31511, when aerobically propagated in an aqueous nutrient medium, produces nocardicin A in good yield.

1 Claim, No Drawings

PROCESS FOR PRODUCING NOCARDICIN A

BACKGROUND OF THE INVENTION

Among the best known and widely used class of antibacterial agents are the so-called β-lactam antibiotics. These compounds are characterized in that they have a nucleus consisting of a 2-azetidinone (β-lactam) ring. When the β-lactam is fused to a thiazolidine ring, the compounds are usually referred to generically as penicillins. When the β-lactam is fused to a dihydrothiazine ring, the compounds are referred to as cephalosporins.

The β-lactam antibiotics are synthesized, for no apparent reason, by only a few microorganisms. All of the organisms recognized to produce β-lactam antibiotics are filamentous microorganisms, but not all of these microorganisms are taxonomically related. Some are fungi (eukaryotes), whereas others are streptomycetes (prokaryotes). Thienamycin, U.S. Pat. No. 3,950,357, is an interesting new β-lactam antibiotic produced by a species of Streptomyces.

Nocardicin A, U.S. Pat. No. 3,923,977, is a novel β-lactam antibiotic produced by Nocardia uniformis var. tsuyamanensis ATCC 21806. Nocardicin A has an unusual β-lactam moiety which is uniquely different from all other β-lactam antibiotics in not being fused to another ring as shown in the following structure:

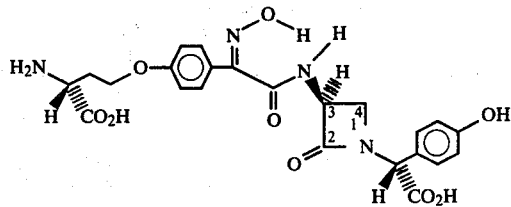

The unique structure of nocardicin A may account for its relative stability toward a variety of β-lactamases as well as for its negligible immunological cross-reactivity with penicillins and cephalosporins.

Unfortunately, the outstanding in vitro and in vivo antimicrobial properties of the penicillins and caphalosporins are not shared by nocardicin A. However, the antibiotic's nucleus, 3-aminonocardicinic acid, of the following structure has been prepared, J. Am. Chem. Soc. 100, 3933 (1978):

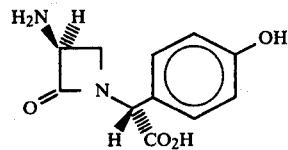

The present invention is concerned with the discovery that nocardicin A is produced by a new species of Nocardiopsis designated Nocardiopsis atra Huang sp. nov. ATCC 31511. The microorganism with its potential for cultural and mutational development offers promise of the production of large amounts of nocardicin A, subsequent cleavage to 3-aminonocardicinic acid and the synthesis of a variety of clinically useful semisynthetic nocardicins paralleling those of the semisynthetic penicillins and cephalosporins.

SUMMARY OF THE INVENTION

Nocardicin A, previously reported β-lactam antibiotic, is produced by the aerobic propagation in aqueous nutrient media of a new species of Nocardiopsis designated Nocardiopsis atra Huang sp. nov. ATCC 31511.

DETAILED DESCRIPTION OF THE INVENTION

The microorganism useful for the production of nocardicin A was isolated from a coil sample from Nomozaki, Japan. This culture, designated Nocardiopsis atra Huang sp. nov., has been deposited in The American Type Culture Collection, Rockville, Md. as the type culture under their accession number ATCC 31511. The permanency of the deposit of this culture at The American Type Culture Collection at Rockville, Md. and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

The culture was planted from a slant into liquid ATCC No. 172 medium and grown for 4 days at 28° C. on a shaker. It was then removed from the shaker, centrifuged for 20 minutes, washed three times with sterile distilled water and planted on media commonly used for identification of members of the Actinomycetales.

The inoculated plates were incubated at 28° C. and records of results were made after suitable incubation time with most of the final results recorded at 14 days. The colors were described in common terminology, but exact color was determined by comparison with color chips from the Color Harmony Manual, fourth edition.

The methods of whole-cell and sugar analyses are those described by Becker, B. et al., Appl. Microbiol., 12, 421-423 (1964) and by Lechevalier, M.P., J. Lab. Clin. Med., 71, 934-944 (1968). Mycolate analyses were performed by the method of Lechevalier, M.P. et al., J. Bacteriol., 105, 313-318 (1971).

The results of chemical tests of whole-cell and cell wall indicated the new culture belonged in the genus Nocardiopsis. For comparison purposes, therefore, culture studies included Nocardia uniformis subsp. tsuyamanesis ATCC 21806 and Nocardiopsis dassonvillei ATCC 23218.

Identification media used for the characterization of the culture and references for their composition are as follows:
1. Tryptone Yeast Extract Broth (ISP #1 medium, Difco).
2. Yeast Extract-Malt Extract Agar (ISP #2 medium, Difco).
3. Oatmeal Agar (ISP #3 medium, Difco).
4. Inorganic Salts—Starch Agar (ISP #4 medium, Difco).
5. Glycerol—Asparagine Agar (ISP #5 medium, Difco).
6. Glycerol—Asparagine Agar (prepared in our lab).
7. Peptone—Yeast Extract Iron Agar (#6 medium, Difco).
8. Gelatin Agar—R. E. Gordon and J. M. Mihm, Jr. Bact. 73: 15-27, 1957.
9. Starch Agar—Ibid.
10. Organic Nitrate Broth—Ibid.

11. Dextrose Nitrate Broth—S. A. Waksman, The Actinomycetes, Vol. 2, medium no. 1. p. 328, 1961, and 3 g dextrose substituted for 30 g sucrose and agar omitted.

12. Potato Carrot Agar—M. P. Lechevalier, Jr. Lab. and Clinical Med. 71: 934–944, 1968 but use only 30 g potatoes, 2.5 g carrots and 20 g agar.

13. 2% Tap Water Agar

14. Czapek-Sucrose Agar—S. A. Waksman, The Actinomycetes, Vol. 2, medium no. 1, p. 328, 1961.

15. Glucose Asparagine Agar—Ibid, medium no. 2, p. 328.

16. Glucose-Yeast Extract Agar—Ibid, medium no. 29, p. 331

17. Emerson's Agar—Ibid, medium no. 28, p. 331.

18. Nutrient Agar—Ibid, medium no. 14, p. 330.

19. Bennet's Agar—Ibid, medium no. 30, p. 331.

20. Gordon and Smith' Tyrosine Agar R. E. Gordon and M. M. Smith, Jr. Bact. 69: 147–150, 1955.

21. Casein Agar—Ibid.

22. Calcium Malate Agar—S. A. Waksman, Bact. Rev. 21: 1–29, 1957.

23. Gauze's #1 Mineral Agar—G. F. Gauze et al. Problems in the Classification of Antagonistic Actinomycetes. English Ed., p. 13, 1957.

24. Gauze's #2 Organic Agar—Ibid.

25. Skim Milk—Difco

26. Cellulose utilization—
   (a) H. L. Jensen, Proc. Linn. Soc. N.S.W. 55: 231–248, 1930.
   (b) M. Levine and H. W. Schoenlein, A Compilation of Culture Media, Medium 2511, 1930.

27. Utilization of Organic Acids—R. E. Gordon et al., Int. Jr. Syst. Bact. 24: 54–63, 1974.

28. Carbohydrate Utilization and Acid Production from Carbohydrates—Ibid.

29. Hydrolysis of Hippurate and Esculin—Ibid.

30. Decomposition of Adenine, Hypoxanthine, Xanthine, and Urea—Ibid.

31. Yeast Dextrose Agar for Studies of Temperature and Survival at 50° C.—Ibid.

32. Resistance to Lysozyme—Ibid.

33. Glucose Broth—Ibid.

| Agar | Cultural Character* | *Nocardiopsis atra* ATCC 31511 | *Nocardia uniformis* subsp. *tsuyamanensis* ATCC 21806 | *Nocardiopsis dassonvillei* ATCC 23218 |
|---|---|---|---|---|
| Yeast Extract-Malt Extract Agar | G | Poor to moderate | Good | Excellent |
| | SC | Brown to greyish brown (4 lg to 4 li) | Orange (4 ia to 4 lc) | White with pale orange tint (3 ea) |
| | T | Thin, smooth to slightly Sc | Thin to slightly raised, wrinkled | Wrinkled with a fluffy edge, |
| | AM | — | — | White |
| | RC | Same as SC | Same as SC | Yellowish orange (3 ia to 3 lc) |
| | SP | — | — | Pale yellowish |
| Oatmeal Agar | G | Moderate | Moderate | Moderate |
| | SC | Dull white | Pale brownish (3 gc) | Colorless to white |
| | T | Thin, smooth, with a few small white dots | Submerged, smooth with spreading edge | Thin, smooth with spreading edge |
| | AM | None to scant | — | White, sparse |
| | RC | Same as SC | Same as SC | Same as SC |
| | SP | Pale greenish | — | — |
| Inorganic Salts-Starch Agar | G | Moderate | Moderate to good | Moderate |
| | SC | Pale grey to greyish (near grey series, 2 dc to 2 fe) with white tint | Yellowish orange (3 ea, 3 ia to 3 la) | White to pale yellowish (2 ga) |
| | T | Thin, smooth | Thin to slightly raised | Thin to slightly raised smooth to slightly wrinkled |
| | AM | White | — | White |
| | RC | Same as surface | Same as surface | Same as surface |
| | SP | Pale greyish green (1 gc) | — | — |
| Glycerol Asparagine Agar (dehydrated powder from Difco) | G | Poor to moderate | Poor to moderate | Poor |
| | SC | Colorless to cream | Colorless to pale yellowish brown (near 2 ea) | Colorless to pale cream |
| | T | Thin, appearing as confluent smear or very small isolated dots | Submerged, smooth | Thin, smooth, with a fluffy edge |
| | AM | — | — | — |
| | RC | Same as surface | Same as surface | Same as surface |
| | SP | — | — | — |
| Glycerol | G | Good | Moderate | Moderate to good |

-continued

| Agar | Cultural Character* | Nocardiopsis atra ATCC 31511 | Nocardia uniformis subsp. tsuyamanensis ATCC 21806 | Nocardiopsis dassonvillei ATCC 23218 |
|---|---|---|---|---|
| Asparagine Agar (Prepared) | SC | Grey, dark grey to black (near grey series, 3 ih to 3 ml) | Orange (3 ga to 3 ia) | White to cream (1 ½ ca) |
| | T | Raised, slightly wrinkled | Thin, smooth, with a spreading edge | Raised, roughened to wrinkled |
| | AM | — | — | White |
| | RC | Brown (4 pg to 4 pi) to black | Same as surface | Pale yellowish to pale yellowish green (1 ½ ea to 1 ½ gc) |
| | SP | Greyish orange (near 3 gc) to black | Very pale orange | Pale yellowish |
| Gelatin Agar | G | Good | Good | Good |
| | SC | Grey to black (near grey series, 3 fe) | Orange (3 ia) | Cream to pale yellowish (2 ca to 2 ga) |
| | T | Raised, wrinkled | Thin, smooth but slightly wrinkled near the edge | Thin, smooth but slightly wrinkled near the end of streak |
| | AM | — | — | White |
| | RC | Same as surface | Same as surface | Yellowish (2 ia) |
| | SP | Greyish | — | — |
| Starch Agar | G | Good | Good | Good |
| | SC | Greyish to black (near grey series 2 ih to 7 ml | Orange (near 4 ia or 4 la) | Yellowish brown (near 2 lc) but white near edge |
| | T | Raised, roughened | Slightly raised, wrinkled | Slightly raised, wrinkled |
| | AM | — | — | White |
| | RC | Same as surface | Same as surface | Same as surface |
| | SP | Greyish | — | — |
| Potato Carrot Agar | G | Moderate | Poor to moderate | Poor to moderate |
| | SC | Cream (1 ½ ca) | Colorless to pale brown (2 ca) | Colorless, white to pale brown (2 ca) |
| | T | Thin, smooth, with some small slightly raised dots | Submerged, thin, smooth, with a spreading edge | Thin, smooth, with a fluffy, spreading edge |
| | AM | None to sparse | — | White |
| | RC | Same as surface | Same as surface | Same as surface |
| | SP | — | — | — |
| Tap Water Agar | G | Poor to moderate | Poor | Poor |
| | SC | Colorless to white | Colorless | Colorless |
| | T | Thin, smooth, with a few white dots | Submerged, smooth, with a spreading edge | Thin, smooth |
| | AM | None to sparse | — | — |
| | RC | Same as surface | Same as surface | Same as surface |
| | SP | — | — | — |
| Czapek-Sucrose Agar | G | Moderate | Moderate | Moderate |
| | SC | Pale greyish green (1 ½ ec) with some small black dots, greyish near the end of streak (near grey series, 2 fe) | Yellowish to yellowish orange (1 ½ ea to 2 lc) | Cream (1 ½ ca) with very pale greenish tint |
| | T | Thin, smooth | Submerged, smooth with a spreading edge | Slightly raised and roughened |
| | AM | — | — | White, sparse |
| | RC | Same as surface | Same as surface | Same as surface |
| | SP | Pale greenish (1 ½ gc) | — | Pale greyish |
| Glucose | G | Moderate | Moderate | Moderate |

-continued

| Agar | Cultural Character* | Nocardiopsis atra ATCC 31511 | Nocardia uniformis subsp. tsuyamanensis ATCC 21806 | Nocardiopsis dassonvillei ATCC 23218 |
|---|---|---|---|---|
| Asparagine Agar | SC | Pale brown (3 gc) to black | Yellowish orange (3 ga to 3 la) | Cream (1 ¼ ca) |
| | T | Slightly raised, smooth, with small raised black dots | Thin, smooth, with a few small raised dots | Thin to slightly raised appearing as small isolated dots, slightly wrinkled |
| | AM | — | — | — |
| | RC | Brown to black | Same as surface | Same as surface |
| | SP | Pale yellowish brown | — | — |
| Glucose Yeast Extract Agar | G | Good | Good | Good |
| | SC | Black (near grey series, 3 po) | Orange (near 4 ia) | White to cream (2 ca) |
| | T | Raised, wrinkled | Slightly raised, wrinkled | Raised, strongly wrinkled |
| | AM | — | — | White |
| | RC | Black | Same as surface | Yellowish brown (near 2 ic) |
| | SP | Black | — | Brown (3 ic) |
| Emerson's Agar | G | Good to excellent | Good | Good |
| | SC | Black (near grey series, 3 ml) | Orange (4 ga to 4 ia) | White, cream to brown (2 ca to 3 le) |
| | T | Raised, wrinkled | Slightly raised, wrinkled, but smooth near the edge | Slightly raised, roughened to wrinkled, with a fluffy, spreading edge |
| | AM | — | — | White |
| | RC | Black | Same as surface | Brown |
| | SP | Black | Yellowish brown (3 lc) | Brown (4 ne) |
| Nutrient Agar | G | Moderate to poor | Moderate | Moderate |
| | SC | Pale grey to grey (near grey series, 2 dc, 2 ih to 2 ml) | Pale orange (between 3 ea 4 ea) | Cream (2 ca) |
| | T | Thin, smooth, with raised black dots | Thin, smooth | Thin, smooth or appearing as small isolated dots, with a spreading edge |
| | AM | — | — | White, sparse |
| | RC | Same as surface | Same as surface | Cream to pale yellowish |
| | SP | Pale greyish | — | — |
| Bennett's Agar | G | Good to excellent | Moderate to good | Good |
| | SC | Black (near grey series, 3 ml) | Yellowish orange (3 ga to 3 la) | Cream to yellowish (2 ca to 2 ea) with a white edge |
| | T | Raised, wrinkled, | Thin, smooth to slightly wrinkled | Moderately raised, wrinkled, with a fluffy edge |
| | AM | — | — | White |
| | RC | Black | Same as surface | Same as surface |
| | SP | Black | — | — |
| Gordon and Smith' Tyrosine Agar | G | Moderate | Moderate to good | Moderate |
| | SC | Grey to dark grey (near grey series, 2 ih to 2 ml) | Dark orange (near 4 lc) | Dirty white |
| | T | Thin to slightly raised, slightly roughened to granular | Thin, smooth | Thin, smooth or appearing as small isolated dots, with a spreading edge |
| | AM | — | — | White |
| | RC | Same as surface | Same as surface | Pale yellowish |
| | SP | Greyish black | Brown (near 3 ic) | Brown (between |

| Agar | Cultural Character* | Nocardiopsis atra ATCC 31511 | Nocardia uniformis subsp. tsuyamanensis ATCC 21806 | Nocardiopsis dassonvillei ATCC 23218 |
|---|---|---|---|---|
| | | | | 3 gc and 3 ic) |
| Calcium Malate Agar | G | Moderate | Poor to moderate | Moderate |
| | SC | Black | Yellowish to yellowish brown (2 ga to 2 lc) | Dirty white to cream (2 ca) |
| | T | Thin, smooth, with some raised dots | Thin, smooth, with a spreading submerged edge | Appearing as isolated dots |
| | AM | — | — | White |
| | RC | Black | Same as surface | Yellowish brown (2 ic) |
| | SP | Pale greenish | — | — |
| Gauze's #1 Mineral Agar | G | Moderate | Moderate to good | Moderate to good |
| | SC | Pale greenish cream | Yellowish orange (3 ea to 3 ia) | White |
| | T | Thin, with small white to greyish dots | Thin, smooth, with a spreading edge | Slightly raised and wrinkled |
| | AM | White, sparse | — | White |
| | RC | Same as surface | Same as surface | Greyish brown (2 ie) |
| | SP | Pale greenish (1 ca) | — | Pale greyish (between 2 ec and 2 ge) |
| Gauze's #2 Organic Agar | G | Moderate to good | Good | Moderate to good |
| | SC | Dark brown to greyish (3 ni, near grey series 3 ih) | Orange (3 ga, 3 ia to 3 gc) | Cream |
| | T | Raised, granular to flaky | Slightly raised, wrinkled, with a moderately spreading edge | Raised and wrinkled |
| | AM | — | — | — |
| | RC | Dark brown to black | Same as surface | Same as surface |
| | SP | Greyish brown | Pale yellowish orange | Pale yellowish |

*G-growth, SC-surface color, T-texture, AM-aerial mycelium, RC-reverse color, SP-soluble pigment, "-" means none.

| Biochemical and Physiological Properties | N. atra ATCC 31511 | Nocardia uniformis subsp. tsuyamanensis ATCC 21806 | Nocardiopsis dassonvillei ATCC 23218 |
|---|---|---|---|
| Gram stain | + | + | + |
| Acid-fastness | — | — | — |
| Decomposition of: | | | |
| Adenine | — | — | + |
| Calcium malate | + | + | + |
| Casein | + | + | + |
| Hypoxanthine | — | — | + |
| Tyrosine | + | — | — |
| Urea | + | + | + |
| Xanthine | — | — | + |
| Hydrolysis of: | | | |
| Esculin | — | + | + |
| Hippurate | + | — | + |
| Starch | + | + | + |
| Growth at: | | | |
| 45° C. | — | — | — |
| 37° C. | very poor | good | good |
| 28° C. | good | good | good |
| 21° C. | very poor | good | good |
| Survival at 50° C. 8 h | — | + | — |
| Melanin production | — | — | — |
| H$_2$S production | — | + | + |
| Gelatin liquefaction | + | + | + |
| Cellulose decomposition | — | — | — |
| Growth in cellulose broth: | | | |
| Jensen's | poor | good | poor |
| Levine & Schoenlein's | — | poor | — |
| Skim milk: | | | |
| Coagulation | — | + | — |
| peptonization | — | + | — |
| Acid from and (utilization of): | | | |
| Adonitol | + (+) | − (−) | − (−) |
| Arabinose | + (+) | + (±) | + (+) |
| Cellobiose | + (+) | + (+) | + (+) |
| Dulcitol | − (−) | − (+) | − (−) |
| Erythritol | − (+) | − (±) | − (−) |
| Fructose | + (+) | + (+) | + (+) |
| Galactose | + (+) | + (+) | + (+) |
| Glucose | + (+) | + (+) | + (+) |
| Glycerol | + (+) | + (+) | + (+) |
| Inositol | + (+) | − (−) | − (−) |
| Lactose | + (+) | + (+) | − (±) |
| Maltose | + (+) | + (+) | + (+) |
| Mannitol | + (+) | + (+) | + (+) |
| Mannose | + (+) | + (+) | + (+) |
| Melezitose | − (±) | − (±) | − (±) |
| Melibiose | + (+) | + (+) | − (−) |

-continued

| Biochemical and Physiological Properties | N. atra ATCC 31511 | Nocardia uniformis subsp. tsuyamanensis ATCC 21806 | Nocardiopsis dassonvillei ATCC 23218 |
|---|---|---|---|
| α-Methyl-d-glucoside | + (+) | − (−) | − (±) |
| Raffinose | + (+) | + (+) | − (±) |
| Rhamnose | + (+) | + (+) | + (+) |
| Ribose | + (+) | − (−) | + (+) |
| Salicin | + (+) | + (+) | + (+) |
| Sorbitol | − (+) | − (±) | − (−) |
| Sorbose | − (±) | − (±) | − (−) |
| Starch | + (+) | + (+) | + (+) |
| Sucrose | + (+) | + (+) | + (+) |
| Trehalose | + (+) | + (+) | + (+) |
| Xylose | + (+) | + (+) | + (+) |
| Utilization of: | | | |
| Acetate | + | + | + |
| Benzoate | − | − | − |
| Citrate | + | − | + |
| Dextrin | − | − | − |
| Lactate | + | + | + |
| Malate | + | + | + |
| Mucate | − | − | − |
| Oxalate | − | − | − |
| Phenol | − | − | − |
| Propionate | − | − | − |
| Pyruvate | + | + | + |
| Succinate | + | + | + |
| Nitrite from Nitrate: | | | |
| Dextrose nitrate broth | − | + | + |
| Organic nitrate broth | − | + | + |
| Resistance to lysozyme | − | + | − |

"+", positive; "−", negative; "±", doubtfully utilized.

Morphological observations were made 1, 2, 3, 5, 7, 14 and 28 days after the inoculation of the new Nocardiopsis culture on Czapek sucrose agar. Substrate mycelium began to fragment into bacillary cells after 3 days of incubation; aerial mycelium appeared after 5 days of incubation; substrate and aerial mycelia fragmented after 14 days of incubation into rods of varying lengths which were smooth and measured 1.5–10 (or longer)×0.6–0.9 μm.

The cell wall contained meso-diaminopimelic acid but not diagnostic sugars. The cell wall contained no mycolates of any kind.

The new culture is characterized by gram-positive reaction, non-acid-fastness, black or greyish colonies, black or greyish colony reverse, black soluble pigment on some media and fragmentation of both aerial and substrate mycelia. These features plus the presence of mesodiaminopimelic acid in the cell wall but the absence of diagnostic sugars and mycolates place the new culture in the genus Nocardiopsis.

The biochemical and physiological properties distinguishing the new culture from Nocardia uniformis subsp. tsuyamanesis are the decomposition of tyrosine; hydrolysis of esculin and hippurate; growth at 21° and 37° C. survival at 50° C. for 8 hours; H₂S production; growth in Jensen's cellulose broth; coagulation and peptonization of milk; nitrate reduction; resistance to lysozyme; acid production after utilization of adonitol, inositol, α-methyl-d-glucoside and ribose. The new culture differs from Nocardiopsis dassonvillei in hydrolysis of esculin; growth at 21° and 37° C.; H₂S production; nitrate reduction; decomposition of adenine, hypoxanthine tyrosine and xanthine; acid production from adonitol, inositol, lactose, melibiose, α-methyl-d-glucoside and raffinose; and utilization of adonitol, erythritol, inositol, melibiose and sorbitol.

The new culture was considered to be a new species of Nocardiopsis and was designated as Nocardiopsis atra Huang sp. nov.

Cultivation of Nocrdiopsis atra Huang sp. nov. ATCC 31511 preferably takes place in aqueous nutrient media at a temperature of 24–36° C. and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cottonseed meal, peanut meal, wheat gluten, soy flour, meat meal and fish meal. A source of growth substances such as grain solubles and yeast extract as well as salts such as sodium chloride and calcium carbonate and trace elements such as iron, zinc, cobalt and maganese may also be utilized with advantageous results. If excessive foaming is encountered during fermentation, antifoam agents such as vegetable oil or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seeded from the shake flasks. Growth in shaken flasks will generally have reached its maximum in 2 to 4 days whereas inoculum in submerged inoculum tanks will usually be at the most favorable period in 1.5–3 days. Substantial antibiotic activity is obtained in the final fermentor stage in approximately 2 to 5 days.

The process of antibiotic production is conveniently followed during fermentation by biological assay of the broth employing a sensitive strain of Comamonas terrigena ATTC 8461 or Micrococcus lutenus. Standard plate assay technique is employed in which the zone of inhibition surrounding a filter paper disc saturated with broth is used as a measure of antibiotic potency.

The antibiotic produced by Nocardiopsis atra Huang sp. nov. ATCC 31511 was recovered from the filtered fermentation broth and purified by a combination of carbon absorption and elution and column chromatography. The antibiotic was established to be identical with previously reported nocardicin A (U.S. Pat. No. 3,923,977) by comparison with the published physicochemical data and side by side comparisons with nocardicin A obtained from the fermentation broth of known producer Nocardia uniformis subsp. tsuyamanensis ATCC 21806.

EXAMPLE 1

A sterile aqueous medium having the following composition is prepared:

| Ingredient | Grams/liter |
|---|---|
| Glucose | 25 |
| Corn steep liquor | 15 |
| Distillers' solubles | 10 |
| Cottonseed meal | 5 |

| Ingredient | Grams/liter |
| --- | --- |
| Cobalt chloride | 0.01 |
| Calcium carbonate | 3 |

Cells from a slant culture of *Nocardiopsis atra* ATCC 31511 are transferred to each of a number of 300 ml shake flasks each containing 40 ml of the above medium and shaken for 3 to 4 days at 28° C.

Aliquots sufficient to provide a 5% v/v inoculum are transferred to fermentors each containing two liters of the above described sterile medium. The temperature is maintained at 30° C. The broth is stirred at 200 r.p.m. and aerated at the rate of about one volume of air per volume of broth per minute. The fermentation is maintained until substantial antibiotic activity is obtained (3–4 days).

Nocardicin A may be recovered and separated by the methods described in U.S. Pat. No. 3,923,977.

EXAMPLE II

The method of Example I may be repeated with comparable results employing a fermentation medium of the following composition:

| Ingredient | Grams/liter |
| --- | --- |
| Glucose | 30 |
| Corn steep liquor | 6 |
| Glycine | 3 |
| Cottonseed meal | 6 |
| DL-methionine | 2 |
| Calcium carbonate | 5 |

EXAMPLE III

The method of Example I may be repeated with comparable results employing a fermentation medium of the following composition:

| Ingredient | Grams/liter |
| --- | --- |
| Glucose | 1 |
| Dextrin | 24 |
| Yeast extract | 5 |
| Beef extract | 3 |
| Polypeptone | 5 |
| Calcium carbonate | 4 |

We claim:

1. A process for producing nocardicin A which comprises aerobically propagating *Nocardiopsis atra* Huang sp. nov. ATCC 31511 in an aqueous nutrient medium containing a source of assimilable carbon and a source of assimilable nitrogen until a substantial amount of nocardicin A is obtained.

* * * * *

UNITED STATES PATENT AND TRADEMARK OFFICE
CERTIFICATE OF CORRECTION

PATENT NO. : 4,212,944
DATED : July 15, 1980
INVENTOR(S) : Walter D. Celmer et al It is certified that error appears in the above-identified patent and that said Letters Patent is hereby corrected as shown below:

In the title page, item "[75]" should include as the last named inventor --and Junsuke Tone, Chita, Japan--.

Signed and Sealed this

Fourteenth Day of February 1984

[SEAL]

Attest:

GERALD J. MOSSINGHOFF

Attesting Officer — Commissioner of Patents and Trademarks